United States Patent [19]
Andrews

[11] Patent Number: 5,810,760
[45] Date of Patent: Sep. 22, 1998

[54] CEREBRAL EDEMA SOLUTE CATHETER AND METHOD OF DRAINING CEREBRAL EDEMA

[75] Inventor: David W. Andrews, Philadelphia, Pa.

[73] Assignee: Thomas Jefferson University, Philadelphia, Pa.

[21] Appl. No.: 694,105

[22] Filed: Aug. 8, 1996

[51] Int. Cl.$^6$ .................................................. A61M 5/00
[52] U.S. Cl. ............................................. 604/8; 604/266
[58] Field of Search ................................ 604/8–10, 48, 604/264, 265, 280, 283, 53, 266, 267, 268, 269

[56] References Cited

U.S. PATENT DOCUMENTS

| | | | |
|---|---|---|---|
| 4,215,695 | 8/1980 | Spitz et al. | 128/350 V |
| 4,434,797 | 3/1984 | Silander | 604/264 |
| 4,531,937 | 7/1985 | Yates | 604/53 |
| 4,685,463 | 8/1987 | Williams | 604/8 |
| 4,790,817 | 12/1988 | Luther | 604/53 |
| 4,923,598 | 5/1990 | Scal | 604/5 |
| 5,327,734 | 7/1994 | White, Jr. | 128/325 |

*Primary Examiner*—John G. Weiss
*Assistant Examiner*—Ki Yong O
*Attorney, Agent, or Firm*—Woodcock Washburn Kurtz Mackiewicz & Norris, LLP

[57] ABSTRACT

Catheters for removing interstitial fluid from a cerebral edema that comprises an edema drainage section terminating in a proximal tip linked to a fluid transport section terminating in a distal tip are disclosed. The edema drainage section comprises an outer wall, an inner drainage tube and an intermediate solute compartment that comprises a solute. Methods of removing fluid from a cerebral edema of an individual are disclosed, and comprise the steps of inserting the edema drainage section of the catheter into communication with the fluid of the cerebral edema and inserting the fluid transport section of the catheter into a fluid receptacle or the individual's peritoneal cavity. The fluid is drawn into the edema drainage section and emerges from the distal tip of the fluid transport section of the catheter.

13 Claims, 3 Drawing Sheets

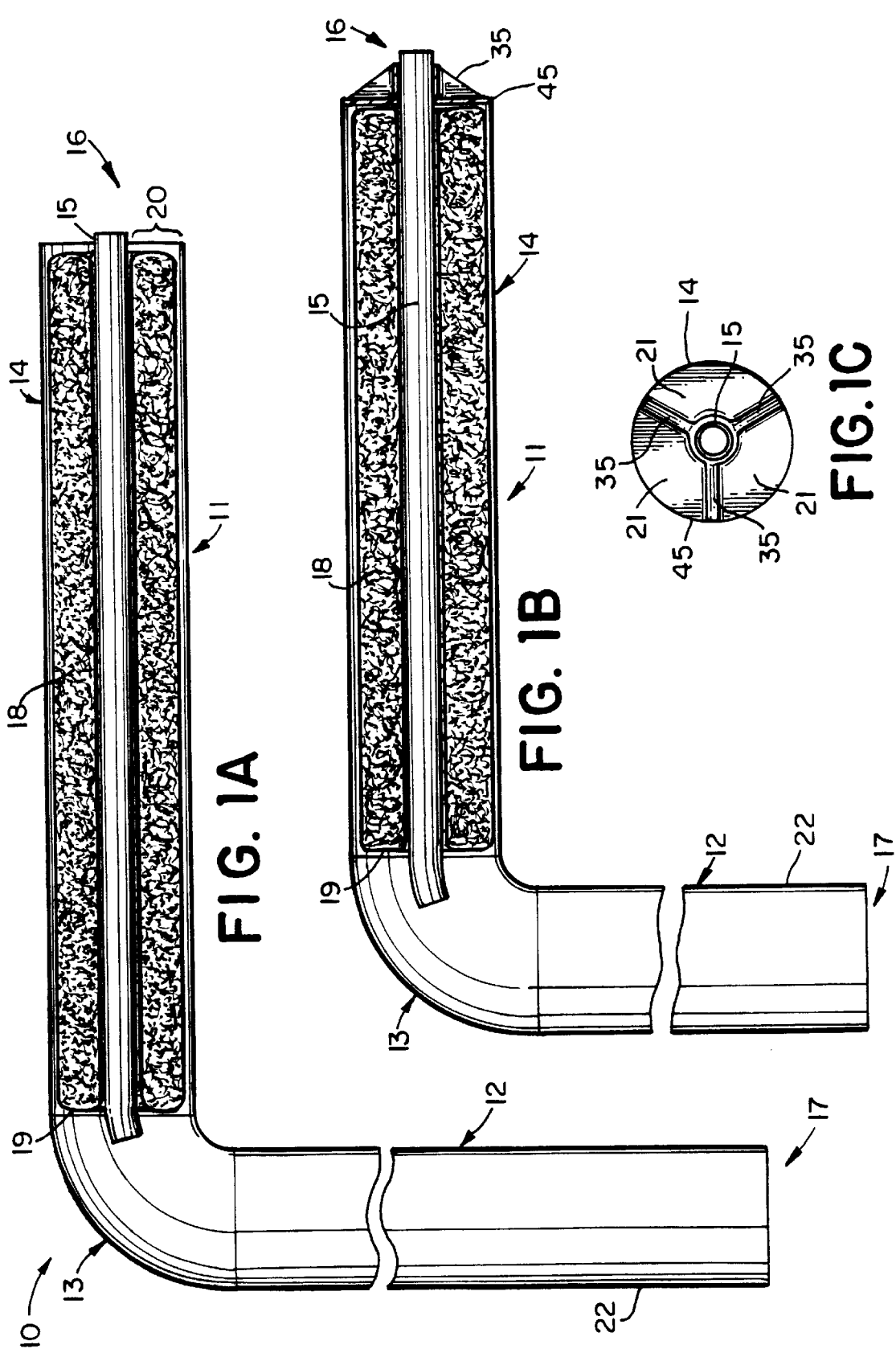

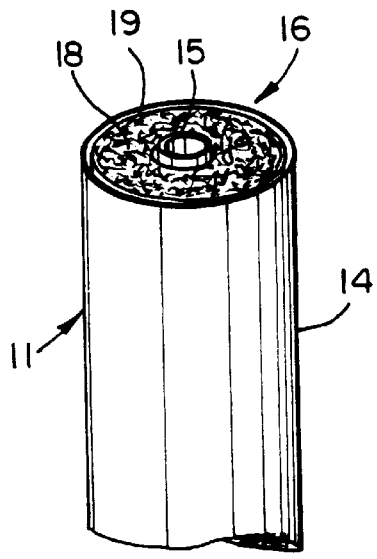
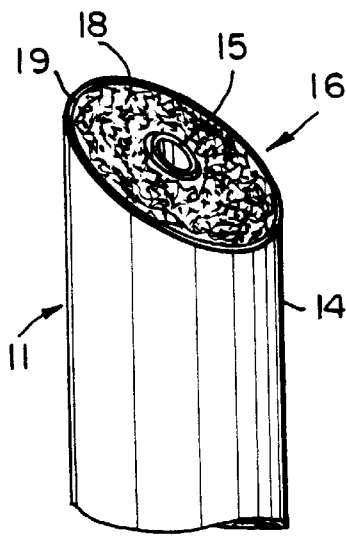
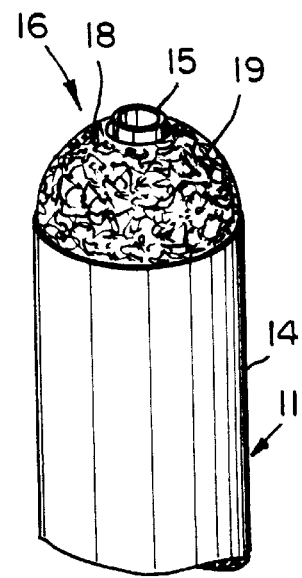
FIG.2A   FIG.2B   FIG.2C
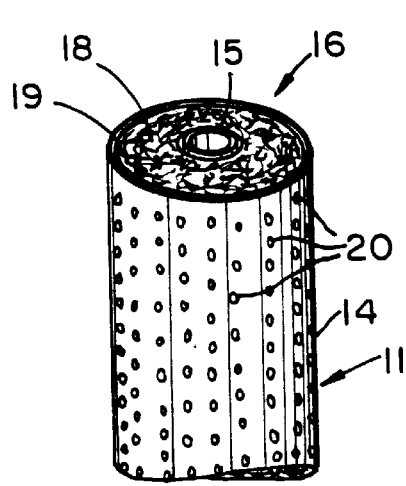
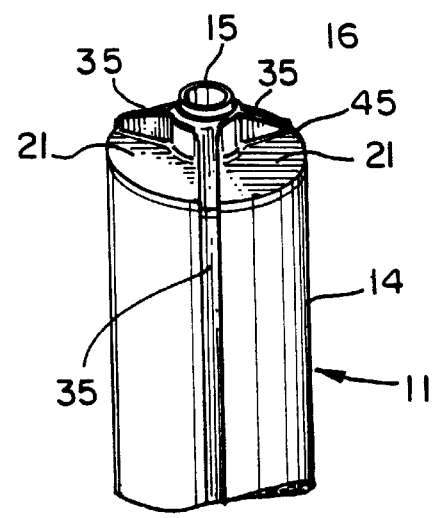
FIG.2D   FIG.2E

CEREBRAL EDEMA SOLUTE CATHETER AND METHOD OF DRAINING CEREBRAL EDEMA

FIELD OF THE INVENTION

The present invention relates to solute drainage catheters and, in particular, to a catheter for draining interstitial fluid from a cerebral edema.

BACKGROUND OF THE INVENTION

Cerebral edema is a type of brain swelling most commonly associated with cerebral trauma or mass lesions, which results in an increase in volume of intracranial contents leading to serious, and sometimes fatal, intracranial pressure. Interstitial (extracellular) fluid, or free water, is abnormal in the brain and accumulates as a result of swelling from a nearby brain tumor, or other type of cerebral lesion. This fluid enters the white matter in the brain due to a compromise of the blood-brain barrier. The fluid can contain small proteins, as well as other small molecular weight molecules, which escape the circulatory system or are a result from the tissue damage itself.

Currently, there is no known approach for removing or draining interstitial fluid from a cerebral edema. Methods exist only for improving the symptoms of swelling due to the accumulation of the fluid. These methods involve the use of oral or intravenous steroids, which have known systemic side effects. For example, the steroid DECADRON™ has only a modest effect on cerebral edema and has systemic side effects including water retention, osteoporosis, aseptic necrosis of the femoral head, capillary fragility with easy bruising, increased appetite, and insomnia.

Prior art fluid draining systems only teach removing cerebrospinal fluid, and other fluids, from ventricles in the brain. These draining systems consist of a shunt which protrudes into the ventricular region, such as a typical catheter described in U.S. Pat. No. 4,215,695, issued to Spitz, et al. In such prior art catheters, the pressure of the cranial cavity serves as the mechanism which moves the cerebrospinal fluid through the catheter to an extracorporeal collection area or other region within the patient's body for disposal. However, sufficient pressure is not present in the region of a cerebral edema to provide for this type of mechanism for transporting interstitial fluid through a ventricle type shunt placed in the region.

Accordingly, a need exists for such an apparatus for draining interstitial fluid from a cerebral edema. The cerebral edema catheter described below provides for the drainage of interstitial fluid from a cerebral edema.

SUMMARY OF THE INVENTION

The present invention is directed to a catheter for removing interstitial fluid from a cerebral edema. The catheter, which is referred to herein as a cerebral edema solute catheter or CES catheter, has an edema drainage section and a transport section. The edema drainage section terminates in a proximal tip. The fluid transport section terminates in a distal tip. The edema drainage section may be linked directly to the transport section or indirectly by intermediate components such as a connector, such that one end of the connector is linked to the edema drainage section and the other end of the connector is linked to the transport section.

The CES catheter may be used as follows. The edema drainage section is inserted into the patient's brain and comes into contact with the interstitial fluid. The fluid enters the edema drainage section, progresses through it and into the transport section. The fluid enters the edema drainage section by first passing through the pores, openings or openings of the outer wall and entering the intermediate solute compartment. The fluid hydrates the solute and passes from the intermediate solute compartment into the inner drainage tube through pores or openings of the inner drainage tube. The fluid passes through the inner drainage tube and into the transport section. The fluid either collects in a fluid receptacle or is discharged into the patient's body. The fluid receptacle may be linked directly to the transport section or linked by way of a junction. The fluid receptacle may be calibrated to measure the amount of fluid drained.

The edema drainage section is inserted into the patient's brain at the site of the edema and comes into contact with the fluid. The edema drainage section has an outer wall, an intermediate solute compartment and an inner drainage tube. The edema drainage section of the CES catheter is inserted into the patient's brain and is positioned to the site in the brain in order to come into contact with the fluid to be removed.

The outer wall of the drainage section is attached at one end directly or indirectly to the transport section. In some embodiments, the outer wall is attached to a connector which is linked to the transport section. In one embodiment of the invention, the outer wall is either porous, such that it has a molecular weight exclusion limit, or it contains an opening so fluid can pass through it and come in contact with the intermediate solute compartment. When the edema drainage section of the CES catheter is inserted into the patient's brain, the outer wall comes into contact with the fluid to be removed. The fluid passes through the pores of, or opening or openings in the outer wall and comes into contact with the intermediate solute compartment.

The intermediate solute compartment separates the inner surface of the outer wall and the outer surface of the inner drainage tube, and contains a solute. The solute can be free, or can be contained within a solute compartment membrane. The solute compartment membrane is porous and preferably is a micropore structure such that water, or fluid, from the edematous area of the brain is able to pass through the solute compartment membrane and into the solute.

The solute comprises large molecular weight macromolecules which are unable to pass through the outer wall and/or the solute compartment membrane and which are capable of being hydrated. Such macromolecules create an osmotic diffusion gradient such that water is drawn into the edema drainage section of the CES catheter through the outer wall at the proximal tip.

The inner drainage tube is a porous, membranous, tube within the CES catheter and surrounded by the outer wall and intermediate solute compartment. In one embodiment of the invention, the inner drainage tube comprises three flanges that radiate from the proximal tip portion of the drainage section and longitudinally traverse the outer wall, thus firming the supporting framework for the outer wall where the outer wall comprises a porous material. The outside of the inner drainage tube is surrounded by the solute compartment membrane or by the solute itself. The area between the outer surface of the inner drainage tube and the outer wall forms the intermediate solute compartment. The inner drainage tube preferably is a water permeable membrane that transports small molecules, such as water, into the lumen of the drainage tube. While not wishing to be bound by theory, this transport of fluid arises from hydrostatic pressure building up in the intermediate solute compartment.

Interstitial fluid, which is drawn through the outer wall and hydrates the solute, passes through the pores of and enters into the inner drainage tube. The inner drainage tube extends through the edema drainage section and may empty directly into the fluid transport section.

The fluid transport section is essentially a tube connected directly or indirectly to the edema drainage section.

The present invention is also directed to a method of removing fluid from a cerebral edema of an individual comprising the steps of inserting the edema drainage section of the cerebral edema solute catheter of the invention into communication with the fluid of the cerebral edema, and inserting the fluid transport section of the cerebral edema solute catheter of the invention into a fluid receptacle or the individual's peritoneal cavity, wherein the fluid is drawn into the edema drainage section and emerges from the distal tip of the fluid transport section of the cerebral edema solute catheter.

BRIEF DESCRIPTION OF THE DRAWINGS

FIGS. 1A and 1B are views of preferred embodiments of the cerebral edema solute catheter. FIG. 1C shows a cross sectional view of the cerebral edema solute catheter show in FIG. 1B.

FIGS. 2A, 2B, 2C, 2D, and 2E show several embodiments of the proximal tip of the cerebral edema solute catheter.

DETAILED DESCRIPTION OF THE PREFERRED EMBODIMENTS

Figure 3:
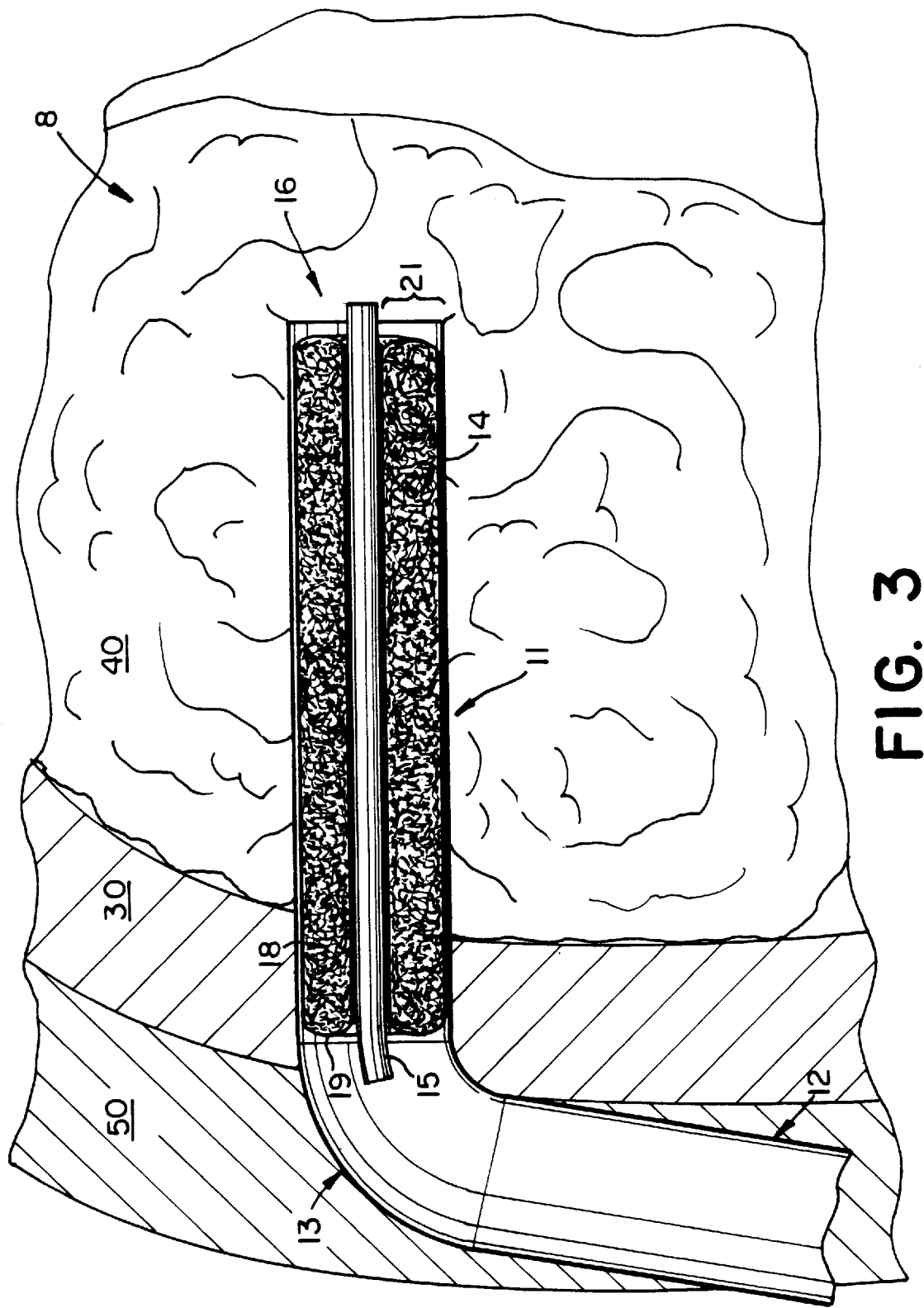
FIG. 3 is a view of the embodiment set forth in FIG. 1A in which the proximal tip of the catheter is in an area of the brain to be drained.

The present invention is directed to a cerebral edema solute catheter (CES catheter) which provides for the drainage of interstitial fluid from a cerebral edema. The cerebral edema solute catheter 10 shown in FIGS. 1A and 1B comprises three regions or sections. The CES catheter 10 comprises a first section, the edema drainage section 11, which drains the fluid from the cerebral edema within the brain The terminal region of the edema drainage section 11 comprises a proximal tip 16 of the cerebral edema solute catheter 10. The CES catheter 10 also comprises a second portion, a fluid transport section 12, which transports the fluid from the edema drainage section 11 of the CES catheter 10 to a receptacle or another region of the body. The terminal region of the fluid transport section 11 comprises a distal tip 17 of the cerebral edema solute catheter 10. The CES catheter 10 may optionally comprise a third section, a connector section 13, which connects the edema drainage section 11 of the CES catheter 10 to the fluid transport section 12 of the CES catheter 10.

The edema drainage section 11 of the cerebral edema solute catheter 10 comprises an outer wall 14, which forms a tube or tube-like structure. The outer wall 14 can be manufactured from a variety of medically accepted plastics or metals, as is well known to those skilled in the art. A preferred plastic is silastic plastic. Such an embodiment wherein the outer wall comprises a silastic plastic is shown in FIG. 1A. The thickness of the outer wall 14 is between 0.001 and 5.0 mm, preferably between 0.01 and 3.0 mm, and more preferably between 0.1 and 1.0 mm. The tube formed by the outer wall 14 can be of uniform diameter throughout the length of the edema drainage section 11 of the cerebral edema solute catheter 10. Alternately, the tube formed by the outer wall 14 can be tapered or enlarged at either end of the edema drainage section 11.

In another embodiment of the invention, as shown in FIG. 1B, the outer wall 14 comprises a porous membrane, such as, for example, dialysis tubing, as is well known to those skilled in the art of dialysis. A preferred membrane is SPECTRAPORE™. The porous membrane which comprises the outer wall 14 preferably is a micropore structure such that water, or fluid, from the edematous area of the brain is able to pass through the outer wall 14 and into the CES catheter 10. Thus, the porous membrane of the outer wall 14 preferably has a molecular weight exclusion limit which is greater than the molecular weight of the fluid to be drained from the cerebral edema. Preferably, the molecular weight exclusion limit of the porous membrane of the outer wall 14 excludes passage of molecules having molecular weights greater than 80,000, more preferably greater than 40,000, and most preferably greater than 12,000. The porous membrane of the outer wall 14 is preferably dialysis tubing with a molecular weight exclusion limit of between about 12,000 and 14,000. In this embodiment, the outer wall 14 is supported as discussed below. The tube formed by the outer wall 14 in this embodiment can be of uniform diameter throughout the length of the edema drainage section 11 of the cerebral edema solute catheter 10. Alternately, the tube formed by the outer wall 14 can be tapered or enlarged at either end of the edema drainage section 11. Preferably, the outer wall 14 of this embodiment is a rounded triangle in cross-section. In either embodiment of the invention, the diameter of the tube formed by the outer wall 14 is between 1.0 mm and 4.0 cm, preferably between 5.0 mm and 3.0 cm, and more preferably between 1.0 cm and 2.0 cm. In addition, the edema drainage section 11 is preferably from about 1.0 cm to about 30.0 cm, more preferably from about 5.0 cm to 20.0 cm, and most preferably is adapted to be an optimum length determined by the distance from the location of the cerebral edema to the outer surface of the skull.

The edema drainage section 11 of the cerebral edema solute catheter 10 also comprises, inside of the tube formed by the outer wall 14, an inner drainage tube 15. Preferably, the inner drainage tube 15 is a single tube. Alternately, the inner drainage tube 15 can be comprised of a plurality of inner drainage tubes. The inner drainage tube 15 can be centrally located within the edema drainage section 11 of the cerebral edema solute catheter 10, or, alternatively, peripherally located within the edema drainage section 11 of the cerebral edema solute catheter 10, such as, for example, in contact with the outer wall 14. The inner drainage tube 15 preferably is a water permeable membrane, such as, for example, hollow fiber tubing produced by AMICON™. Alternately, the inner drainage tube 15 can be made of other membranes, such as, for example, water permeable membranes. The inner drainage tube 15 preferably only allows transport of small molecules, such as water, into the lumen of the inner drainage tube 15. Preferably, the inner drainage tube 15 extends only through the entire length of the edema drainage section 11 of the cerebral edema solute catheter 10, however, the inner drainage tube 15 may only partially extend through the edema drainage section 11. Alternately, the inner drainage tube 15 can extend into the fluid transport section 12 of the cerebral edema solute catheter 10 or into an intermediate component which is linked to the fluid transport section 12 of the cerebral edema solute catheter 10, such as a connector section 13 which is linked to the fluid transport section 12 of the cerebral edema solute catheter 10. The thickness of the wall of the inner drainage tube 15 is preferably between 0.001 and 1.0 mm, and more preferably between 0.01 and 0.1 mm. The diameter of the inner drainage tube 15 is preferably between 1.0 mm and 2.0 cm, and more preferably between 5.0 mm and 1.0 cm. The inner drainage tube 15 can be of uniform diameter throughout the length of the edema drainage section 11 of the cerebral edema solute catheter 10. Alternately, the inner drainage tube 15 can be tapered or enlarged at either end of the edema drainage section 11 of the CES catheter 10. In some embodiments of the invention, the inner drainage tube 15 is closed at the proximal tip 16. That is, the lumen of the inner drainage tube 15 at the proximal tip 16 of the edema drainage section 11 of the CES catheter 10 is not in contact with the edema. In alternate embodiments, the inner drainage tube 15 is open.

In another embodiment of the invention, as shown in FIG. 1B, the inner drainage tube 15 comprises a plurality, preferably three, of flanges 35. The flanges 35 may be comprised of a silastic plastic or the like. The flanges 35 are either continuous with the inner drainage tube 15, or alternately, the flanges 35 are connected to the inner drainage tube by a variety of means well known to the skilled artisan. FIG. 1C shows a cross sectional view of the edema drainage section 11 of the CES catheter as shown in FIG. 1B, showing the inner drainage tube 15, the outer wall 14, and the flanges 35. In this embodiment, the area between the flanges 35 creates the intermediate solute compartment 21, which is filled with solute 18 (not shown). The flanges 35 form the supporting framework for the outer wall 14, wherein the outer wall 14 comprises a porous membrane. The outer wall 14 is connected to the flanges 35 by conventional means known to those skilled in the art.

The edema drainage section 11 of the cerebral edema solute catheter 10 also comprises, in the space between the outer wall 14 of the edema drainage section 11 and the inner drainage tube 15, an intermediate solute compartment 21 that contains a solute 18. The solute 18 is either exists free within the intermediate solute compartment 21, and thus is encompassed by the outer wall 14, or is enclosed within an intermediate solute compartment membrane 19. The intermediate solute compartment membrane 19 preferably is a micropore structure such that water, or fluid, from the edematous area of the brain is able to pass through the intermediate solute compartment membrane 19 and into the solute 18. Thus, the intermediate solute compartment membrane 19 preferably has a molecular weight exclusion limit which is greater than the molecular weight of the fluid to be drained from the cerebral edema. Preferably, the molecular weight exclusion limit of the intermediate solute compartment membrane 19 excludes passage of molecules having molecular weights greater than 80,000, more preferably greater than 40,000, and most preferably greater than 12,000. The intermediate solute compartment membrane 19 is preferably dialysis tubing with a molecular weight exclusion limit of between about 12,000 and 14,000. Preferably, the intermediate solute compartment membrane 19 comprises the same porous membrane as the porous membrane of the outer wall 14 in some embodiments of the invention, such as the embodiment shown in FIG. 1B.

The solute 18 comprises large molecular weight macromolecules which are capable of being hydrated. Such macromolecules create an osmotic diffusion gradient such that water is drawn into the edema drainage section 11 of the CES catheter 10 through the proximal tip 16, or through the outer wall 14 comprising a porous membrane, or through a combination thereof. Preferably, the molecular weight of the solute 18 is from 100,000 to 1,000,000, more preferably from 300,000 to 750,000, and most preferably is 500,000. The solute 18 can be, for example, agarose, cellulose, polystyrene, proteins, dextran, apoferritin, or other large molecular weight macromolecules, or a combination thereof. Preferably, the solute 18 is dextran or apoferritin. Preferably the solute 18 is in a 1% to 50% solution with water, and most preferably is in a 10% solution. The most preferred solute 18 is a 10% solution of dextran having a molecular weight of 500,000. The solute 18 has a molecular weight such that is it unable to pass through the intermediate solute compartment membrane 19 and/or the openings or pores of the outer wall 14 and inner drainage tube 15.

The intermediate solute compartment 21, and thus the solute 18 and intermediate solute compartment membrane 19, preferably extend through the entire length of the edema drainage section 11 of the cerebral edema solute catheter 10. However, it is contemplated that the intermediate solute compartment 21 may only be partially filled with the intermediate solute compartment membrane 19 containing the solute 18. The intermediate solute compartment 21 is located peripherally to the inner drainage tube 15. However, it is conceived that only the terminal section of the edema drainage section 11 of the CES catheter 10 may comprise the intermediate solute compartment 21. Alternately, the intermediate solute compartment 21 can extend into the optional connector section 13 or through the connector section 13 and into the fluid transport section 12 of the cerebral edema solute catheter 10. Preferably, the intermediate solute compartment 21 is filled with the solute 18 such that there is no space between the intermediate solute compartment 21 and the outer wall 14 or between the intermediate solute compartment 21 and the inner drainage tube 15. That is, preferably, the intermediate solute compartment 21 is filled with solute 18 so as to force the solute 18 or solute compartment membrane 19 to be in contact with both the outer wall 14 and the drainage tube 15. However, such spaces can exist as a result of, for example, incompletely filling the intermediate solute compartment 21 with solute 18. It is preferred that the solute 18 within the intermediate solute compartment 21 is within an intermediate solute compartment membrane 19 and that the intermediate solute compartment membrane 19 is continuous and thus forms an intermediate solute compartment 21 entirely encompassing the solute 18. To this end, it can be necessary to seal both ends of the solute compartment membrane 19 when, for example, dialysis tubing is used. Sealing the ends of the dialysis tubing can be accomplished, for example, by clamping means, heat-sealing means, or other forms of sealing known to those skilled in the art.

The edema drainage section 11 of the CES catheter 10 terminates at the proximal tip 16. By "proximal" is meant the tip of the CES catheter 10 closest to the cerebral edema. The proximal tip 16 can take the form of several structural designs, as shown in FIGS. 2A, 2B and C, all of which provide for contact between the cerebral edematous tissue and the CES catheter 10. In a first embodiment, shown in FIG. 2A, the intermediate solute compartment membrane 19 containing the solute 18 is flush with the proximal tip 16, in which the opening of the proximal tip 16 is at a right angle with the outer wall 14. That is, the intermediate solute compartment membrane 19 does not protrude beyond the outer wall 14 of the edema drainage section 11 of the CES catheter 10. In this embodiment, the inner drainage tube 15 is also flush with the proximal tip 16. This type of proximal tip 16 is referred to as a flush proximal tip.

In another embodiment of the invention, shown in FIG. 2B, the proximal tip 16 is beveled, such as, for example, in a syringe needle. The proximal tip 16 in this embodiment can be angled at any desirable angle. The inner drainage tube 15 can extend beyond the opening created by the beveled proximal tip 16, or, alternately, can be flush with the opening. The inner drainage tube 15 can also be beveled in a similar manner to that of the proximal tip 16. In addition, the intermediate solute compartment membrane 19 containing the solute 18 is flush with the beveled proximal tip 16. This type of proximal tip 16 is referred to as a beveled proximal tip.

In another embodiment of the invention, shown in FIG. 2C, the intermediate solute compartment membrane 19 containing the solute 18 extends beyond the proximal tip 16. The proximal tip 16 can be such that the opening of the proximal tip 16 is at a right angle with the outer wall 14, as in FIG. 2A, or, alternately, the proximal tip 16 can be beveled, such as in FIG. 2B. In any case, the intermediate solute compartment membrane 19 containing the solute 18 can form a bulb-like projection extending beyond the outer wall 14. The intermediate solute compartment membrane 19 preferably extends beyond the outer wall 14 from between about 0.1 mm and 10.0 cm, more preferably from between about 1.0 mm and 2.0 cm, and most preferably between about 1.0 mm and 1.0 cm. The inner drainage tube 15 can extend as far as the intermediate solute compartment membrane 19, such that the inner drainage tube 15 is flush with the end of the intermediate solute compartment membrane 19. Alternately, the inner drainage tube 15 terminates within the bulb-like region of the intermediate solute compartment membrane 19, or remains flush with the end of the outer wall 14. A proximal tip 16 having any of these types of configurations is referred to as bulb proximal tip.

In other embodiments of the invention, any of the proximal tips heretofore described can be perforated with drainage vents 20 within the outer wall 14, as illustrated in FIG. 2D. The drainage vents 20 can be of any shape or size such that the integrity of the outer wall 14 is maintained. The drainage vents 20 can be within the outer wall 14 along the entire length of the edema drain section 11 of the catheter 10, or, alternatively, can be restricted to the terminal region of the edema drainage section 11.

In another embodiment of the invention, shown in FIG. 2E, the proximal tip 16 of the CES catheter 10 comprises a cap 45. Such a proximal tip 16 embodiment is preferably used in connection with the embodiment of the CES catheter as shown in FIG. 1B. The cap 45 preferably is comprised of a silastic plastic, such as the same material as comprises the flanges 35, as set forth above. The cap 45 is incorporated in and is continuous with the flanges 35 of the inner drainage tube 15 (not shown). Alternately, the cap 45 is a separate piece and is attached to the flanges 35 and outer wall 14 by conventional means well known to the skilled artisan. In embodiments of the catheter, such as the embodiment shown in FIG. 1B, where the outer wall 14 comprises a porous membrane and the solute 18 is free within the intermediate solute compartment 21, cap 45 is preferred. However, in embodiments of the catheter, such as the embodiment shown in FIG. 1B, where the outer wall 14 comprises a porous membrane and the solute 18 is within the intermediate solute compartment 21 but enclosed within a intermediate solute compartment membrane 19, any of the embodiments of FIGS. 2A, 2B, or 2C can be used. A proximal tip 16 having the type of configuration shown in FIG. 2E is referred to as a cap proximal tip.

The edema drainage section 11 of the CES catheter 10 may be connected to a connector section 13 at the end of the edema drainage section 11 distal to the proximal tip 16. The connector section 13 connects the edema drainage section 11 of the CES catheter 10 to the fluid transport section 12 of the CES catheter 10 such that the fluid drained from the cerebral edema passes from the edema drainage section 11 through the connector section 13 and into the fluid transport section 12. The connector section 13 can form any angle connecting the edema drainage section 11 and the fluid transport section 12. Preferably, the connector section forms a 90° angle. The connector section 12 of the CES catheter 10 can be a separate piece distinct from either the edema drainage section 11 or the fluid transport section 12. In this case, the connector section 13 can comprise female or male sections such that the connector section 13 screws into the appropriate end of either the edema drainage section 11 or the fluid transport section 12, which also comprise a female or male counterpart, as needed. In an alternate embodiment, the inside diameter of the connector section 12 is such that the connector section slips over the ends of the edema drainage section 11 or the fluid transport section 12. Alternately, the outside diameter of the connector region is such that it slips inside the ends of the edema drainage section 11 or the fluid transport section 12. A sealer can be used in these cases to provide for additional sealing. In another embodiment of the invention, the connector section 13 of the catheter 10 is formed continuously with either or both of the edema drainage section 11 and the fluid transport section 12. That is, the connector section 13 is not a separate and distinct piece of the catheter 10.

The fluid transport section 12 of the CES catheter 10 is attached to the connector section 13 as described above. The fluid transport section 12 also comprises a catheter wall 22, which forms a tube, as in the case of the edema drainage section 11. The catheter wall 22 of the fluid transport section 12 can be manufactured from a variety of medically accepted plastics or metals, as is well known to those skilled in the art. A preferred plastic is silastic plastic. The thickness of the catheter wall 22 is between 0.001 and 5.0 mm, preferably between 0.01 and 3.0 mm, and more preferably between 0.1 and 1.0 mm. The diameter of the tube formed by the catheter wall 22 is between 1.0 mm and 4.0 cm, preferably between 5.0 mm and 3.0 cm, and more preferably between 1.0 cm and 2.0 cm. The tube formed by the catheter wall 22 can be of uniform diameter throughout the length of the fluid transport section 12 of the cerebral edema solute catheter 10. Alternately, the tube formed by the catheter wall 22 can be tapered or enlarged at either end of the fluid transport section 12. The fluid transport section 12 is preferably from about 1.0 cm to about 200.0 cm, more preferably from about 50.0 cm to 150.0 cm, and most preferably is adapted to be an optimum length determined by the distance from the connector section 13 to the peritoneal cavity of a patient.

The fluid transport section 12 terminates at a distal tip 17. The distal tip 17 can be of the same diameter as the fluid transport section 12 or can be expanded or reduced. In a preferred embodiment of the invention, the distal tip 17 empties the fluid from the cerebral edema into the peritoneal cavity. In another embodiment of the invention, the distal tip 17 of the fluid transport section 12 of the CES catheter 10 is connected to a shunt (not shown) in the abdominal wall of a patient, which in turn is further connected to a distensible storage compartment (not shown), such as, for example, a colostomy bag, which can be emptied as needed.

The cerebral edema solute catheter 10 is preferably used in humans, although the catheter can also be used in a variety of other mammals. The apparatus of the present invention can be used to drain interstitial fluid from a cerebral edema. The CES catheter 10 is inserted into the brain of an individual comprising an edema The skull of an individual is opened and the edema located using routine surgical procedures known to those skilled in the art. The edema drainage section 11 of the CES catheter 10 is inserted into the brain such that the proximal tip 16 is placed into the edematous mass. Thus, the proximal tip 16 is in communication with the fluid to be drained. An enlarged view of the edema drainage section 11 of the CES catheter 10 inserted into the edematous fluid, or interstitial fluid, 8 of the brain 40 is shown in FIG. 3. The connector section 13 is located at the outside layer of the skull 30 and is connected to the fluid transport section 12 of the CES catheter 10 which in turn is located between the skull 30 and the overlying scalp tissue 50. The fluid transport section 12 of the CES catheter 10 is fed, between the skull and the scalp by routine surgical techniques, preferably behind the ear into the neck and through the chest section of the individual to the peritoneal cavity. Alternate routes of placement can be used as known to those skilled in the art. It is understood that any embodiment of the CES catheters described herein can be used in the methods of removing fluid from cerebral edemas described herein.

The concentration gradient of the solute 18 within the intermediate solute compartment membrane 19 or free within the intermediate solute compartment 21 creates an osmotic gradient such that the fluid from the edema is drawn into the edema drainage section 11 of the CES catheter 10. The fluid passes through the outer wall 14 or the intermediate solute compartment membrane 19, or both, and hydrates the solute 18. The influx of fluid from the edema into the area of the solute 18 causes an expansion of the solute 18 until a maximum expansion is achieved, at which time the pressure within the edema drainage section 11 of the catheter 10 causes the fluid to pass from the intermediate solute compartment 21 into the inner drainage tube 15. Thus, the fluid passes from the edema to the inside of the edema drainage section 11 of the catheter 10 as a result of the osmotic gradient facilitated by the solute 18. The inner drainage tube 15 then acts as a release mechanism in which the fluid is able to be drained from the edema drainage section 11 of the CES catheter 10. The fluid then passes through the inner drainage tube 15, into the connector section 13, and into the fluid transport section 12, where it emerges from the distal tip 17 and into the peritoneal cavity. Thus, the CES catheter 10 as depicted in FIG. 1 is a self-contained system that will continually drain interstitial fluid or free water from the edematous tissue of the brain of a patient into another body compartment for disposal.

From the foregoing it can be seen that the present invention is directed to a catheter for draining interstitial fluid or free water from a cerebral edema. It is understood that changes may be made to the embodiments described above without departing from the broad inventive concepts thereof. Accordingly, this invention is not limited to the particular embodiments disclosed, but is intended to cover all modifications that are within the scope and spirit of the invention.

What is claimed is:

1. A catheter for removing fluid from a cerebral edema comprising:
   an edema drainage section terminating in a proximal tip that is constructed and arranged to be positioned within an area of cerebral edema, said edema drainage section comprising:
   an outer wall;
   an inner drainage tube surrounded by said outer wall; and
   an intermediate solute compartment positioned immediately adjacent to said proximal tip and surrounding said inner drainage tube, wherein said intermediate solute compartment comprises an intermediate solute compartment membrane containing a solute comprising large molecular weight macromolecules; and
   a fluid transport section linked to said edema drainage section, whereby said fluid transport section terminates in a distal tip.

2. The catheter of claim 1 wherein said edema drainage section is linked to said fluid transport section by a connector section.

3. The catheter of claim 1 wherein said proximal tip is selected from the group consisting of a flush proximal tip, a beveled proximal tip, and a bulb proximal tip.

4. The catheter of claim 3 wherein:
   said intermediate solute compartment membrane has a molecular weight exclusion limit greater than the molecular weight of the fluid of said cerebral edema;
   said inner drainage tube is a water permeable membrane; and
   said solute comprises large molecular weight macromolecules capable of being hydrated and having a molecular weight greater than the molecular weight exclusion limit of said solute compartment membrane.

5. The catheter of claim 4 wherein:
   said solute compartment membrane has a molecular weight exclusion limit greater than 12,000;
   said inner drainage tube is hollow fiber tubing; and
   said solute is a macromolecule having a molecular weight from 100,000 to 1,000,000.

6. The catheter of claim 5 wherein:
   said intermediate solute compartment membrane is dialysis tubing, and
   said solute is selected from the group consisting of agarose, cellulose, polystyrene, proteins, dextran, apoferritin, and other large molecular weight macromolecules, or a combination thereof.

7. The catheter of claim 6 wherein said solute is a 10% solution of dextran having a molecular weight of 500,000.

8. The catheter of claim 1 wherein:
   said outer wall is a porous membrane; and
   said inner drainage tube further comprises a plurality of flanges supporting said outer wall.

9. The catheter of claim 8 wherein:
   said edema drainage section is linked to said fluid transport section by a connector section;
   said porous membrane has a molecular weight exclusion limit greater than the molecular weight of the fluid drained from the cerebral edema;
   said inner drainage tube is a water permeable membrane; and
   said solute comprises large molecular weight macromolecules capable of being hydrated and having a molecular weight greater than the molecular weight exclusion limit of said porous membrane.

10. The catheter of claim 9 wherein:
    said porous membrane has a molecular weight exclusion limit greater than 12,000;
    said inner drainage tube is hollow fiber tubing; and
    said solute is a macromolecule having a molecular weight from 100,000 to 1,000,000.

11. The catheter of claim 10 wherein:
    said porous membrane is dialysis tubing, and
    said solute is selected from the group consisting of agarose, cellulose, polystyrene, proteins, dextran, apoferritin, and other large molecular weight macromolecules, or a combination thereof.

12. The catheter of claim 11 wherein said solute is a 10% solution of dextran having a molecular weight of 500,000.

13. A shunt and a catheter for removing fluid from a cerebral edema comprising:
an edema drainage section terminating in a proximal tip that is constructed and arranged to be positioned within an area of cerebral edema, said edema drainage section comprising:
an outer wall;
an inner drainage tube surrounded by said outer wall; and
an intermediate solute compartment positioned immediately adjacent to said proximal tip and surrounding said inner drainage tube, wherein said intermediate solute compartment comprises an intermediate solute compartment membrane containing a solute; and
a fluid transport section linked to said edema drainage section, whereby said fluid transport section terminates in a distal tip connected to said shunt;
wherein said shunt is further connected to a distensible storage compartment.

* * * * *